US012766328B2

(12) United States Patent
Weiss et al.

(10) Patent No.: US 12,766,328 B2
(45) Date of Patent: Oct. 20, 2026

(54) METHOD FOR FABRICATING AN IMPLANTABLE MEDICAL DEVICE WITH A SIMPLIFIED INTERCONNECTION SCHEME AND CORRESPONDING IMPLANTABLE MEDICAL DEVICE

(71) Applicant: BIOTRONIK SE & Co. KG, Berlin (DE)

(72) Inventors: Ingo Weiss, Berlin (DE); Thomas Doerr, Berlin (DE); Thomas Pieske, Berlin (DE)

(73) Assignee: BIOTRONIK SE & Co. KG, Berlin (DE)

( * ) Notice: Subject to any disclaimer, the term of this patent is extended or adjusted under 35 U.S.C. 154(b) by 224 days.

(21) Appl. No.: 18/565,134

(22) PCT Filed: Jul. 1, 2022

(86) PCT No.: PCT/EP2022/068221
§ 371 (c)(1),
(2) Date: Nov. 29, 2023

(87) PCT Pub. No.: WO2023/006336
PCT Pub. Date: Feb. 2, 2023

(65) Prior Publication Data

US 2024/0261578 A1 Aug. 8, 2024

(30) Foreign Application Priority Data

Jul. 28, 2021 (EP) .................................... 21188140

(51) Int. Cl.
*A61N 1/375* (2006.01)

(52) U.S. Cl.
CPC ....... *A61N 1/37512* (2017.08); *A61N 1/3758* (2013.01)

(58) Field of Classification Search
CPC .. A61N 1/37512; A61N 1/3758; A61N 1/375; H05K 1/189
See application file for complete search history.

(56) References Cited

U.S. PATENT DOCUMENTS 5,741,313 A 4/1998 Davis et al.
6,658,296 B1 12/2003 Wong et al.
(Continued)

OTHER PUBLICATIONS

EP Search Report mailed on Jan. 25, 2022, by the European Patent Office for Application No. EP21188140.4. (10 pages).
(Continued)

*Primary Examiner* — Eugene T Wu
(74) *Attorney, Agent, or Firm* — Buchanan Ingersoll & Rooney PC

(57) ABSTRACT

Method for fabricating an implantable medical device comprising:

providing a housing, an electronic module and a plurality of periphery components, the electronic module comprises module contacts for inputting/outputting electric energy to/from the electronic module, each periphery component comprises component contacts for inputting/outputting electric energy to/from the periphery component;

arranging the electronic module and the periphery components in a first configuration wherein each component contact of each periphery component is positioned at a same initial distance relative to a corresponding module contact;

displacing the electronic module and the periphery components by the initial distance relative to each other into a second configuration in which all component contacts of each periphery component directly mechanically contact respective corresponding module contacts;

(Continued)

fixing the electronic module and the periphery components in the second configuration;
accommodating the electronic module and the plurality of periphery components in the housing.

15 Claims, 7 Drawing Sheets

(56) References Cited

U.S. PATENT DOCUMENTS

| | | | | |
|---|---|---|---|---|
| 2003/0048621 | A1* | 3/2003 | Blood | H05K 1/189<br>361/803 |
| 2004/0174658 | A1 | 9/2004 | Ophelan et al. | |
| 2007/0232119 | A1* | 10/2007 | Sprain | A61N 1/3754<br>439/357 |
| 2012/0151758 | A1* | 6/2012 | Primavera | A61N 1/3758<br>29/761 |
| 2013/0079600 | A1 | 3/2013 | Engmark et al. | |
| 2013/0333925 | A1* | 12/2013 | Sporon-Fiedler | H05K 1/0278<br>29/830 |
| 2020/0086131 | A1 | 3/2020 | Henschel | |

OTHER PUBLICATIONS

International Search Report (PCT/ISA/210) and Written Opinion (PCT/ISA/237) mailed on Sep. 14, 2022, by the European Patent Office as the International Searching Authority for International Application No. PCT/EP2022/068221. (16 pages).

* cited by examiner

METHOD FOR FABRICATING AN IMPLANTABLE MEDICAL DEVICE WITH A SIMPLIFIED INTERCONNECTION SCHEME AND CORRESPONDING IMPLANTABLE MEDICAL DEVICE

CROSS-REFERENCE TO RELATED APPLICATIONS

This application is the United States National Phase under 35 U.S.C. § 371 of PCT International Patent Application No. PCT/EP2022/068221, filed on Jul. 1, 2022, which claims the benefit of European Patent Application No. 21188140.4, filed on Jul. 28, 2021, the disclosures of which are hereby incorporated by reference herein in their entireties.

TECHNICAL FIELD

The present invention relates to a method for fabricating an implantable medical device and to a corresponding implantable medical device.

BACKGROUND

Generally, an implantable medical device may be any device which, in an implanted state, provides for a diagnostic and/or therapeutic function within the patient, such as a stimulation function, a sensing function, a monitoring function, a recording function and/or the like. The implantable medical device may be a device configured for cardiac applications such as a pacemaker or a cardiac stimulation device. However, it is not limited to cardiac applications, but, for example, may also be used for neuro-applications.

An implantable medical device may, for example, have the shape of a leadless stimulation device, such as a leadless pacemaker device. In this case a housing of the leadless pacemaker device encapsulates components of the leadless pacemaker device such as a processor, a data memory, a battery and other processing equipment to allow for operation of the leadless pacemaker device in an autarkic manner. The leadless pacemaker device may be implanted directly into a heart and may operate within the heart, for example within the right ventricle of the heart, without requiring any leads for placing an electrode at a location of interest within the heart.

The implantable medical device may also be a stimulation device which comprises a generator to be implanted, for example, subcutaneously at a location remote from the heart. In this case, e.g., a lead extends from the generator into the heart to allow for a stimulation or a sensing of signals at a location of interest within the heart, for example within the right ventricle.

An implantable medical device of this kind, for example a cardiac stimulation device such as a subcutaneous CRT device or a leadless pacemaker device, generally shall be implanted into the patient over a prolonged period of time, such that the implantable medical device remains operative within the patient over its lifespan. For this purpose, the implantable medical device generally comprises an electronic module for implementing or controlling the intended therapeutic or diagnostic function. Furthermore, the medical device electrical typically comprises a plurality of periphery components, e.g., for implementing or controlling specific functions within the medical device. Such a periphery component may be, for example, an energy storage device in the form of a battery or a capacitor or a plurality of such devices, which shall power the implantable medical device for its operation. Alternatively or additionally, electrical resistances serving, e.g., as a dump, coils serving, e.g., as programming coils, antennas serving, e.g., for transmitting and/or receiving signals, signalising elements such as sound generators, vibrators, etc., shielding elements for shielding against electromagnetic fields, feedthrough elements and/or other elements may serve as periphery components.

Generally, all these periphery components may have to be electrically connected to the electronic module. Accordingly, electrical interconnections between module contacts at the electronic module and component contacts at each of the periphery components are required.

Implantable medical devices generally shall be small in built such that they are easily implantable, for example subcutaneously or directly within the patient's heart or in another vessel of interest. This requires all components comprised in the implantable medical device as well as their arrangement within the implantable medical device to be compact and space-efficient. Furthermore, the components shall generally be mounted within the medical device with minimum installation efforts while at the same time ensuring highly reliable installation of all components.

Conventionally, the electrical components, i.e., the electronic module and the periphery components, are accommodated within a common housing in a manner such as to minimise a required volume within the housing. For such purpose, each of the periphery components is, for example, arranged at a suitable available space within the housing and its component contacts are then electrically connected to corresponding module contacts of the electronic module using, for example, electrically conductive connection tapes, bands or connectors.

However, electrically connecting each of the periphery components to the electronic module may require substantial interconnection efforts, materials, space and costs both upon fabricating the implantable medical device as well as with regards to the final device.

The present disclosure is directed toward overcoming one or more of the above-mentioned problems, though not necessarily limited to embodiments that do.

SUMMARY

It is an object of the present invention to provide a method for fabricating an implantable medical device and a fabricated implantable medical device which allow to beneficially reducing interconnection efforts, materials, space and costs. Specifically, it may be an object of the present invention to provide a method for fabricating an implantable medical device and an implantable medical device allowing for a compact construction, a long lifespan, a high reliability and/or an easy manufacturing and assembling of the implantable medical device.

At least such object(s) may be met with the subject-matter of the independent claims. Advantageous embodiments are defined in the dependent claims as well as the corresponding specification and figures.

According to a first aspect of the present invention, a method for fabricating an implantable medical device is proposed. The method comprises at least the following steps, preferably in the indicated order:

providing a housing, an electronic module and a plurality of periphery components, wherein the electronic module comprises module contacts for inputting electric energy to the electronic module and/or outputting electric energy from the electronic module, and wherein each of the periphery components comprises component contacts for inputting electric energy to the periphery component and/or outputting electric energy from the periphery component;

arranging the electronic module and the plurality of periphery components in a first configuration in which each of the component contacts of each of the periphery components is positioned at a same initial distance in relation to a corresponding one of the module contacts with regards to a common direction;

displacing the electronic module and the plurality of periphery components by the initial distance relative to each other in a common motion into a second configuration in which all of the component contacts of each of the periphery components simultaneously directly mechanically contact their respective corresponding module contacts;

fixing the electronic module and the plurality of periphery components in the second configuration; and accommodating the electronic module and the plurality of periphery components in the housing.

According to a second aspect of the present invention, an implantable medical device comprising a housing, an electronic module and a plurality of periphery components is proposed. The electronic module comprises module contacts for inputting electric energy to the electronic module and/or outputting electric energy from the electronic module. Each of the periphery components comprises component contacts for inputting electric energy to the periphery component and/or outputting electric energy from the periphery component. The electronic module and the plurality of periphery components are fixed to each other. All of the component contacts of each of the periphery components directly mechanically contact respective corresponding module contacts. The electronic module comprises at least one buckling portion having reduced buckling rigidity as compared to neighboring portions of the electronic module. At least one of the periphery components is fixed to the electronic module at a position at a first lateral side of the buckling portion and at least one other of the periphery components is fixed to the electronic module at a position at a second lateral side of the buckling portion.

Ideas underlying embodiments of the present invention may be interpreted as being based, inter alia, on the following observations and recognitions.

Briefly summarised in a non-limiting manner, embodiments of the method for fabricating the implantable medical device presented herein may particularly simplify a procedure of assembling and electrically interconnecting components of the medical device. Specifically, the periphery components shall be initially arranged in a first configuration such that preferably all of their component contacts are at a same distance in relation to module contacts of the electronic module, this same distance being measured in a direction being common for all of the contacts. Accordingly, upon starting from such first configuration, the electronic module and the periphery components may be easily displaced relative to each other in a common motion such that each of the component contacts comes into mechanical contact with an associated one of the module contacts. Due to the specific relative arrangement of the electronic module and the periphery components in the first configuration, a second configuration may be achieved by the common motion such that each component contact simultaneously and directly mechanically contacts the respective corresponding module contact. This means that, e.g., no further interconnection means such as interconnecting tapes, bands or connectors are required. Particularly, instead of establishing electrical connections at both ends of an interconnection means, only a single interconnection is required for electrically connecting a module contact to a component contact, as both contacts shall not be interconnected indirectly but directly. Thus, a number of the interconnection processes may be reduced to half, as compared to conventional assembling procedures. Accordingly, the procedure of assembling and electrically interconnecting components of the medical device may be accomplished with less steps and less components. Thereby, a highly automated fabrication procedure may be supported. Furthermore, as all contacts may be arranged in a coplanar configuration, they may have a same distance and/or orientation with regard to an interconnection device such as a welding or soldering machine. In case of the interconnections being established using plug-in connectors or similar means, assembling the periphery components to the electronic module may preferably be realised with a single linear motion.

The medical device may be configured for being implanted into a human or animal body. Its size and shape may be adapted for being inserted into and accommodated in living tissue, e.g., in an available space or cavity in the body. The medical device may be configured for operating autonomously, i.e., without requiring energy from external sources.

The housing may form an outer shell of the medical device. It may enclose all components of the medical device including, inter-alia, the electronic module and the plurality of periphery components as well as, for example, other components such as sensors, electrodes, etc. The housing may enclose the components in a tight, preferably hermetically sealed manner. The housing may be made from a sufficiently stable, non-corrosive material such as stainless steel or a plastic material. The housing may be made with a sheet material. The housing preferably has a rounded shape. This means that at least some portions of the outer surface of the housing preferably have a rounded contour, i.e., are neither planar nor have sharp edges. The rounded portions of the housing may be curved in one or two dimensions. A curvature radius of the rounded portions may be in a same or similar order of magnitude of the dimensions of the housing. Due to the preferably rounded shape of its housing, the medical device may easily and without risks for injuries be inserted and accommodated in living tissue of the body.

The electronic module of the medical device may comprise electronic devices and/or circuitries configured for implementing and/or controlling functionalities of the medical device. For example, the electronic module may comprise a processor, a controller, data memory, a voltage transformer, a sensor, an electrode and/or other electronic devices for realizing therapeutic and/or diagnostic functionalities. The electronic module may comprise a carrier substrate such as a printed circuit board (PCB) supporting and interconnecting the electronic devices mounted at the PCB.

The periphery components of the medical device may be components which support, cooperate and/or interact with the electronic module for establishing the functionalities of the medical device. Particularly, the periphery components may serve for supporting or enabling the autonomous operability of the medical device.

For example, the periphery components may be energy storage devices. Such energy storage devices may be, for example, primary batteries, i.e., non-rechargeable batteries, secondary batteries, i.e., rechargeable batteries, and/or capacitors. An energy storage capacity of such energy storage devices may be adapted for supplying enough electrical energy for the operation of the medical device during a typical lifespan of the medical device of, for example, several months or several years. Each of the periphery components is electrically connected to the electronic module.

For establishing the electrical connection between the periphery components and the electronic module, each periphery component comprises at least two component contacts and the electronic module comprises a number of module contacts, the number corresponding to at least twice the number of periphery components of the medical device. The component contacts and module contacts are typically exposed such as to be accessible from outside the periphery components or electronic module, respectively. Therein, each of the module contacts is associated to one of the component contacts. A positional arrangement of the component contacts substantially corresponds to a positional arrangement of the associated module contacts. Accordingly, upon correctly positioning one of the periphery component relative to the electronic module, its component contacts may coincide, i.e., at least partially overlap, with the module contacts. Thus, the component contacts may directly contact, i.e., without any intermediate interconnection means, the module contacts.

Upon fabricating the implantable medical device, the electronic module and the plurality of periphery components are initially arranged in a first configuration. In such configuration, the periphery components are positioned relative to the electronic module such that its component contacts are spaced apart from the associated module contacts and specifically such that a distance between the component contact and the associated module contact is substantially identical for all pairs of component contacts and module contacts. Therein, the distance is measured in a direction which is common for all pairs of contacts. The term "common direction" may be interpreted in that a first distance between a first module contact and an associated first component contact and a second distance between a second module contact and an associated second component contact is measured along paths being parallel to each other.

In a next step, the electronic module and the periphery components are displaced relative to each other into a second configuration. Therein, for example the electronic module may be displaced towards the stationary periphery components or, vice versa, all of the periphery components may be displaced towards the stationary electronic module or, as a third option, both the electronic module and the periphery components may be displaced towards each other. The displacement is established in a manner such that the relative displacement is accomplished in a common motion in which the initial distance between the module contacts and the component contacts is successively reduced until each module contact directly mechanically contacts its corresponding associated component contact. Preferably, the common motion is adapted such that all module contacts are contacting their corresponding associated component contacts simultaneously. The common motion is preferably a linear motion.

Having reached the second configuration, the electronic module and the plurality of periphery components are fixed relative to each other. Particularly, some or preferably each of the module contacts may be fixed at the corresponding component contacts.

In such fixed configuration, the electronic module and the plurality of periphery components are then accommodated in the housing.

According to an embodiment, in the second configuration, all of the component contacts are arranged in a common plane.

In other words, the electronic module is preferably configured such that its module contacts are all arranged in a single plane. Accordingly, upon having reached the second configuration, the component contacts directly mechanically contacting these module contacts are also arranged in the same plane.

Such configuration of the electronic module and arrangement of the periphery components may be beneficial with regard to a use of any tools, such as, for example, a welding tool, provided for generating, for example, a fixation between the module contacts and the component contacts. With all contacts being arranged in a common plane, such tools may have to be displaced only within this plane, thereby possibly simplifying any tool operation and/or tool displacement.

According to an embodiment, the electronic module comprises a planar carrier substrate and all of the module contacts are arranged at a surface of the carrier substrate.

Expressed differently, the electronic module may comprise a planar substrate such as a printed circuit board (PCB). Such substrate may carry various electronic devices such as a processor, the memory, resistances, capacitors, sensors, etc. for implementing or controlling the therapeutic and/or diagnostic functionalities of the medical device. Furthermore, all module contacts may be arranged at a surface of such planar substrate. Accordingly, all module contacts are arranged in a common plane, thereby enabling the above-mentioned benefits.

According to an embodiment, at least some of the component contacts and the corresponding module contacts are permanently fixed to each other, preferably by one of welding, soldering, crimping and riveting.

In other words, upon fixing the electronic module and the periphery components to each other, at least some or alternatively all of the component contacts are permanently fixed to their corresponding module contacts. Such permanent fixation is generally irreversible, i.e., may not be released without damaging the contacts. The permanent fixation may be established using a positive substance jointing. The permanent fixation may be easy to establish, may not require any additional fixation components and/or may be cost-effective.

For example, the permanent fixation may be established using welding, soldering, crimping, riveting or similar techniques.

Alternatively or additionally, according to an embodiment, at least some of the component contacts and the corresponding module contacts are fixed to each other in a releasable manner, preferably by one of plugging, spring clipping, screwing and snapping-in.

The releasable fixation is generally non-permanent, i.e., the fixation may be established and released reversibly. Accordingly, if required, the electronic module and the periphery components may be reversibly disassembled. However, additional fixation components such as plug connectors, spring clip connectors, screws and/or snap-in connectors may be required, thereby possibly increase manufacturing and logistics efforts.

According to an embodiment, in the first configuration, at least some of the periphery components are held by a holding arrangement comprising frames, each frame being adapted for holding a corresponding one of the periphery components in a form-fitting manner.

In other words, while being arranged in the first configuration, some or preferably all of the periphery components may be held by frames forming the holding arrangement. Therein, a periphery component may be included in a frame in a form-fitting manner. Accordingly, the frame may hold the periphery component reliably while, for example, displacing it from the first configuration to the second configuration. The frame may be adapted such as to enable selectively releasing the periphery component when, for example, reaching the second configuration and/or after the periphery component being fixed to the electronic module.

Alternatively or additionally, according to an embodiment, in the first configuration, at least some of the periphery components are held by a holding arrangement comprising grabbers, each grabber being adapted for selectively grabbing and releasing a corresponding one of the periphery components.

Thus, the holding arrangement may hold and/or displace each of the periphery components using specific grabbers. Therein, a grabber may initially grab and hold the periphery component in its first configuration, may then be displaced together with the periphery component to the second configuration and may release the periphery component when, for example, reaching the second configuration and/or after the periphery component being fixed to the electronic module. Using such grabbers, assembling the periphery components may be implemented with a high degree of automation. For example, one or more same grabbers may simultaneously or sequentially grab, hold and/or displace various periphery components, the periphery components potentially differing with regard to their outer dimensions and/or other characteristics.

According to a further specified embodiment, motions of the grabbers are controlled by a vision system.

For example, the vision system may comprise a camera for optically detecting, e.g., a periphery component and its relative positioning with regard to the electronic module and/or with regard to the grabber. Accordingly, using information from the vision system, the grabber may be controlled such as to grab the periphery component, bring it to the first configuration and/or displace it to the second configuration. Accordingly, a reliable and highly automated positioning of the periphery component may be established.

According to an embodiment, the holding arrangements comprise tolerance elements being configured in a positioning tolerant manner such as to guide the periphery component from the first configuration to the second configuration while allowing an acceptable positioning tolerance.

In other words, the holding arrangements such as the frames or grabbers may additionally comprise elements referred to herein as tolerance elements. These tolerance elements may be specifically configured to establish guiding the periphery component from the first configuration to the second configuration in a position tolerant manner. Due to such position tolerant manner, a motion path of the periphery component may slightly deviate from a motion path of the holding arrangement. Accordingly, the tolerance element may allow an acceptable positioning tolerance such that, for example, a component contact may reach an intended position where it coincides with the corresponding module contact although the holding arrangement would displace the periphery component to a second configuration in which the component contact and the module contact would be slightly offset with respect to each other. For example, the tolerance element may be implemented with elastic elements being interposed somewhere between the frame or a grabber, on the one side, and the periphery component, on the other side.

According to an embodiment, upon the displacing of the electronic module and the plurality of periphery components into the second configuration, guiding structures are provided for guiding the module contacts and the component contacts into coinciding positions.

The guiding structures may be arranged and configured such that, upon the module contact approaching the corresponding component contact, both contacts are guided with respect to each other to positions in which they directly abut to each other. At such coinciding positions, the contacts may then be fixed to each other. The guiding structures may be provided temporarily, i.e., may be arranged at the electronic module and/or the periphery component only during accomplishing the displacement to the second configuration and are removed subsequently. Accordingly, the guiding structures are no more present in the final medical device. Alternatively, the guiding structures may be provided permanently at one or each of the electronic module and the periphery component. Accordingly, the guiding structures are also present in the final medical device. The guiding structures may, for example, have sliding surfaces along which one of the contacts may slide to the position coinciding with the respective other contact.

According to an embodiment, the method furthermore comprises a step of deforming the electronic module with the plurality of periphery components fixed thereto in the second configuration into a third configuration. Therein, in the third configuration, at least one of the periphery components is arranged at another position relative to the electronic module as compared to the second configuration.

In other words, after the periphery components having been fixed to the electronic module, an arrangement of at least one of the periphery components may be modified once more order to change the second configuration to a third configuration. In this third configuration, the position and possibly the orientation of the at least one of the periphery components differs from the second configuration. Accordingly, while the electronic module and the periphery components have been arranged in the second configuration such that, for example, a fixing procedure for fixing the module contacts to the component contacts may be simplified, an entity including the electronic module and the periphery components may subsequently be modified to the third configuration, in which, for example, an arrangement of the electronic module and the periphery components is optimised for subsequently being accommodated within the housing.

For example, according to a further specified embodiment, the electronic module with the plurality of periphery components fixed thereto is deformed into the third configuration by bending at least one portion of the electronic module.

Due to such bending procedure, a portion of the electronic module may be rearranged to another position and orientation and, thus, a periphery component attached to this portion of the electronic module is displaced accordingly. The bending procedure may be easily accomplished after all periphery components have been fixed to the electronic module. Accordingly, the entire arrangement of the electronic module and the plural periphery components may be easily handled as an entity.

According to a further specified embodiment, the electronic module comprises at least one buckling portion having reduced buckling rigidity as compared to neighboring portions of the electronic module. Therein, the electronic module with the plurality of periphery components fixed thereto is deformed into the third configuration by bending the at least one buckling portion.

For example, the electronic module may comprise a carrier element such as a PCB, which, in a spatially limited area, has a reduced rigidity as compared to adjacent areas. Accordingly, such area may serve as a buckling portion. Due to the provision of such buckling portion, the carrier element of the electronic module may be easily and precisely bent upon applying bending forces. Such bending forces may, for example, be applied to different portions of the carrier element at opposite sides with regard to the buckling portion. Due to its reduced rigidity, the buckling portion will be deformed as a result of such bending forces.

The buckling portion may be generated in various manners. For example, a thickness of the carrier element of the electronic module may be reduced locally at the buckling portion in comparison to neighbouring portions. Alternatively or additionally, recesses, through-holes, perforations or similar means may be provided at the buckling portion for reducing its buckling rigidity. As another alternative, the buckling portion may be provided with a material which is more flexible than a material of neighbouring portions.

The implantable medical devices according to an embodiment of the second aspect of the present invention may be fabricated by a method according to an embodiment of the first aspect of the present invention.

Particularly, the electronic module of such medical device may be characterised by having at least one buckling portion and by at least one of the periphery components being fixed to the electronic module at a first lateral side of the buckling portion whereas another one of the periphery components is fixed to the electronic module at a position at a second lateral side of the buckling portion. In other words, periphery components are fixed to the electronic module at both of opposite sides of the buckling portion.

Therein, for example a carrier element of the electronic module may be planar at each of first and second portions at the first and second lateral sides of the buckling portion. However, the buckling portion may be non-planar, i.e., curved. Accordingly, the first and second portions of the carrier element may extend in different planes at an angle with respect to each other, i.e., they may be arranged in different orientations.

According to an embodiment, the electronic module with the plurality of periphery components fixed thereto is configured such that it may be deformed by bending the at least one buckling portion into a configuration in which all of the component contacts are arranged in a common plane.

In other words, a final configuration of the medical device may potentially be modified by bending the at least one buckling portion. Therein, the electronic module and the periphery components shall be arranged and fixed to each other such that, as a result of such bending procedure, all of the component contacts are arranged in a common plane. Such characteristics may be a direct result of the fabrication method applied for fabricating the medical device, wherein during such fabrication method, the electronic module had been deformed by bending the buckling portion from the second configuration to the third, final configuration.

It shall be noticed that the applicant of the present application filed further applications simultaneously with the present application. These further applications have the titles "Implantable medical device with a compact construction" and "Implantable medical device with a space efficient electrical interconnection structure". Embodiments of an implantable medical device are described in these further applications and features and characteristics of such embodiments may be applied or adopted to embodiments of the implantable medical device described in the present application. Accordingly, the content of the further applications shall be incorporated herein in their entirety by reference.

It shall be noted that possible features and advantages of embodiments of the present invention are described herein with respect to various embodiments of a method for fabricating an implantable medical device, on the one hand, and a resulting implantable medical device, on the other hand. One skilled in the art will recognize that the features may be suitably transferred from one embodiment to another and features may be modified, adapted, combined and/or replaced, etc. in order to come to further embodiments of the present invention.

In the following, advantageous embodiments of the present invention will be described with reference to the enclosed drawings. However, neither the drawings nor the description shall be interpreted as limiting the present invention.

Additional features, aspects, objects, advantages, and possible applications of the present disclosure will become apparent from a study of the exemplary embodiments and examples described below, in combination with the Figures and the appended claims.

DETAILED DESCRIPTION

The figures are only schematic and not to scale. Same reference signs refer to same or similar features.

Figure 1:
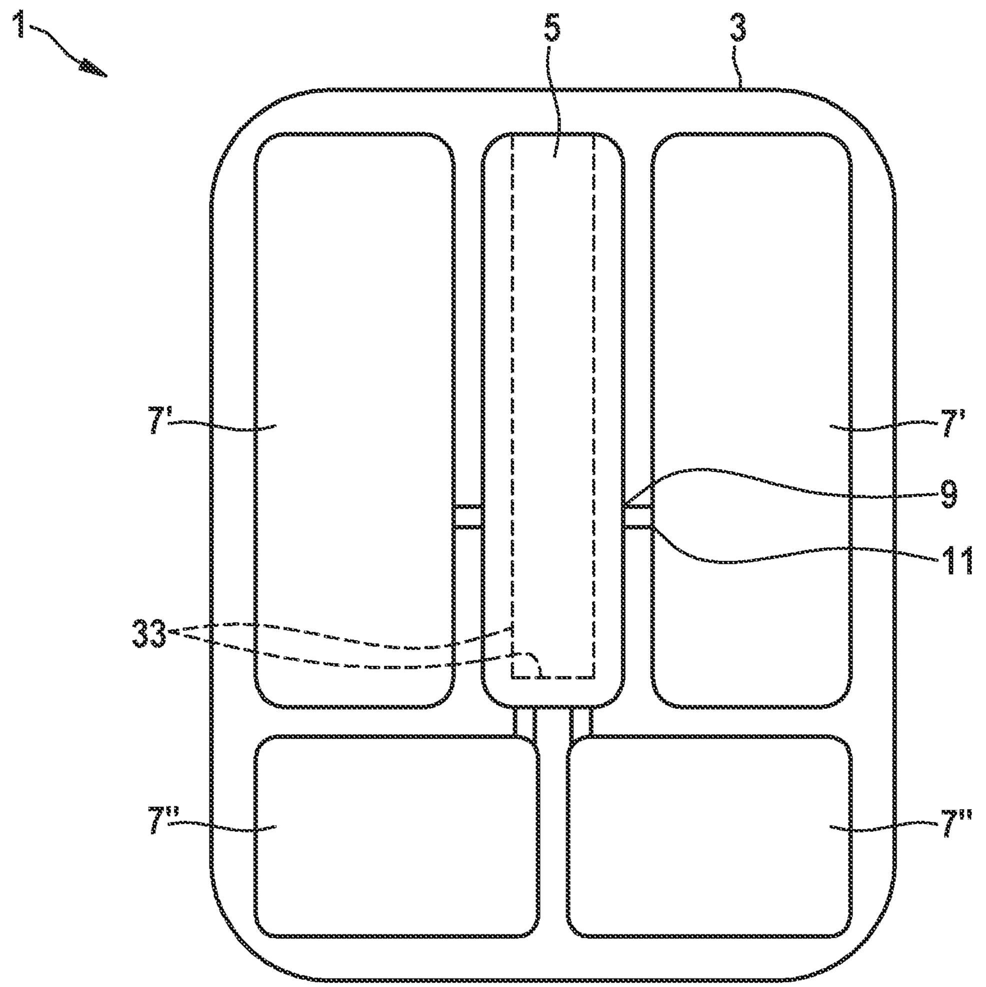
FIG. 1 very schematically shows a representation of an implantable medical device according to an embodiment of the present invention.

FIG. 1 shows a schematic representation of an embodiment of an implantable medical device 1. The medical device 1 comprises a housing 3 in which an electronic module 5 and plural periphery components 7 are accommodated. Each of the periphery components 7 comprises component contacts 11 contacting module contacts 9 at the electronic module 5, thereby being electrically connected to the electronic module 5.

In the represented example, two different types of periphery components 7', 7" are included in the housing 3, the periphery components 7' of a first type having another geometry than the periphery components 7" of a second type. For example, periphery components 7' of the first type may be capacitors, whereas periphery components 7" may be batteries. In the example, two identical periphery components 7' of the first type and two identical periphery components 7" of the second type are comprised in the common housing 3.

Figure 2A:
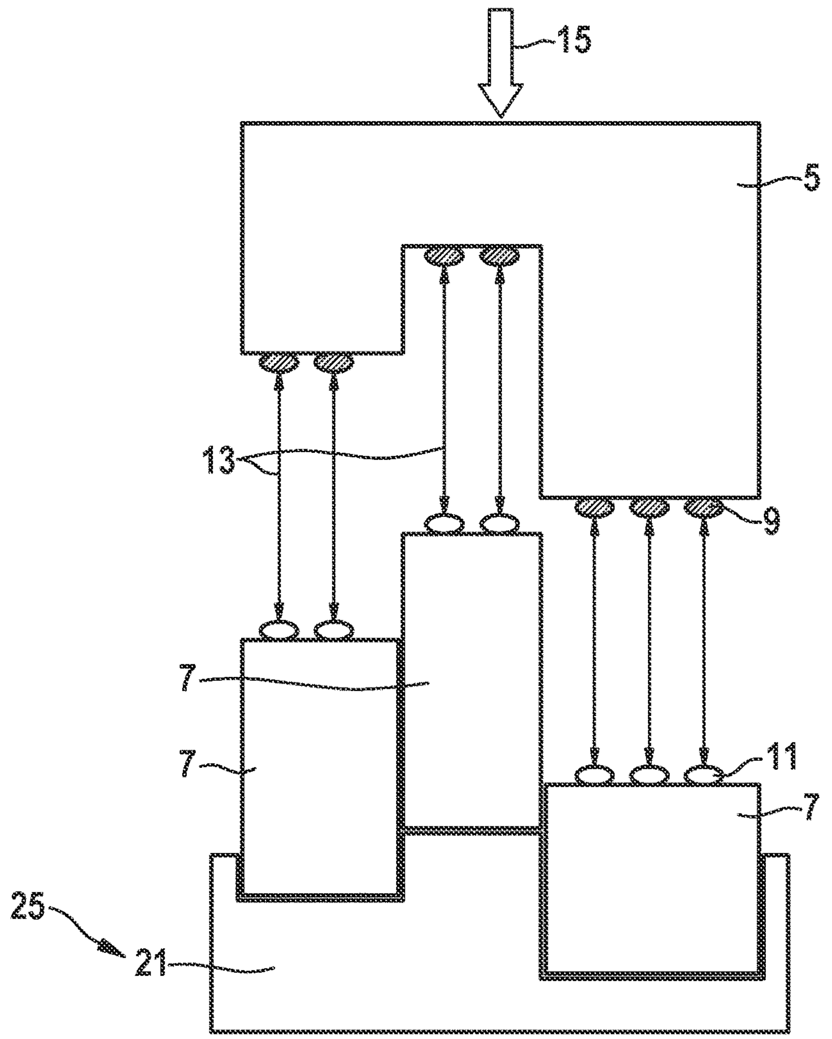
FIGS. 2A-2B show side views onto first configurations during a fabrication method according to embodiments of the present invention.

FIGS. 2A and B schematically represents situations during a method for fabricating an implantable medical device 1.

In FIG. 2A, an electronic module 5 and three different periphery components 7 have been provided. In a horizontal direction, lateral positions of component contacts 11 at the various periphery components 7 are aligned with lateral positions of corresponding module contacts 9 at the electronic module 5. In a vertical direction, each of the periphery components 7 is positioned at a height such that initial distances 13 between the component contacts 11 and the corresponding module contacts 9 are equal for each of the periphery components 7. Therein, the initial distances 13 are all measured in a common direction 15 which, in the visualised example, is the vertical direction.

In the example of FIG. 2A, the periphery components 7 are held by a frame 21 serving as a holding arrangement 25. Therein, the frame 21 comprises cavities, each cavity having a size and contour being complementary to one of the periphery components 7 to be held thereby. Accordingly, the frame 21 may hold each of the periphery components 7 in a form-fitting manner.

By displacing the electronic module 5 and/or the holding arrangement 25 vertically along the direction 15 towards each other, the periphery components 7 and the electronic module 5 may be displaced from the first configuration shown in the figure to a second configuration, in which all of the component contacts 11 of each of the periphery components 7 directly mechanically contact their respective corresponding module contacts 9 at the electronic module 5.

Figure 2B:
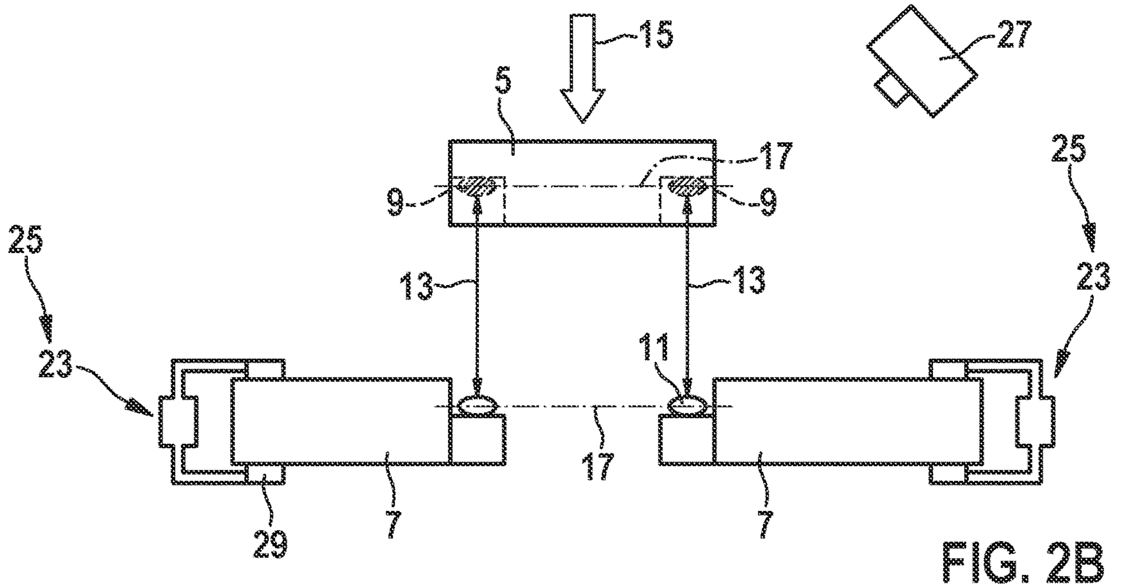

FIG. 2B shows another example in which the electronic module 5 and two periphery components 7 are configured such that their module contacts 9 and component contacts 11 are each arranged in one of parallel common planes 17. Again, initial distances 13 between the component contacts 11 and the corresponding module contacts 9 are equal for each of the periphery components 7 as measured in the common direction 15.

In the example shown in FIG. 2B, each of the periphery components 7 is held by a grabber 23 serving as the holding arrangement 25. Each grabber 23 may selectively grab a corresponding one of the periphery components 7 in a first configuration. Subsequently, the electronic module 5 may be displaced in the common direction 15 towards the periphery components 7 or, alternatively, all grabbers 23 may displace their periphery components 7 in a common motion vertically towards the electronic module 5, until the component contacts 11 directly abut to the module contacts 9. Motions may be monitored using a vision system 27 including a camera and providing some image analysis functionality.

Each grabber 23 comprises tolerance elements 29 formed, for example, by flexible elastomer blocks being interposed between an actuator of the grabber 23 and the grabbed periphery component 7. Due to these tolerance elements 29, the grabber 23 may position the periphery components 7 in a positioning tolerant manner. Accordingly, the periphery components 7 may be displaced from the first configuration to the second configuration while allowing an acceptable positioning tolerance.

Figure 3:
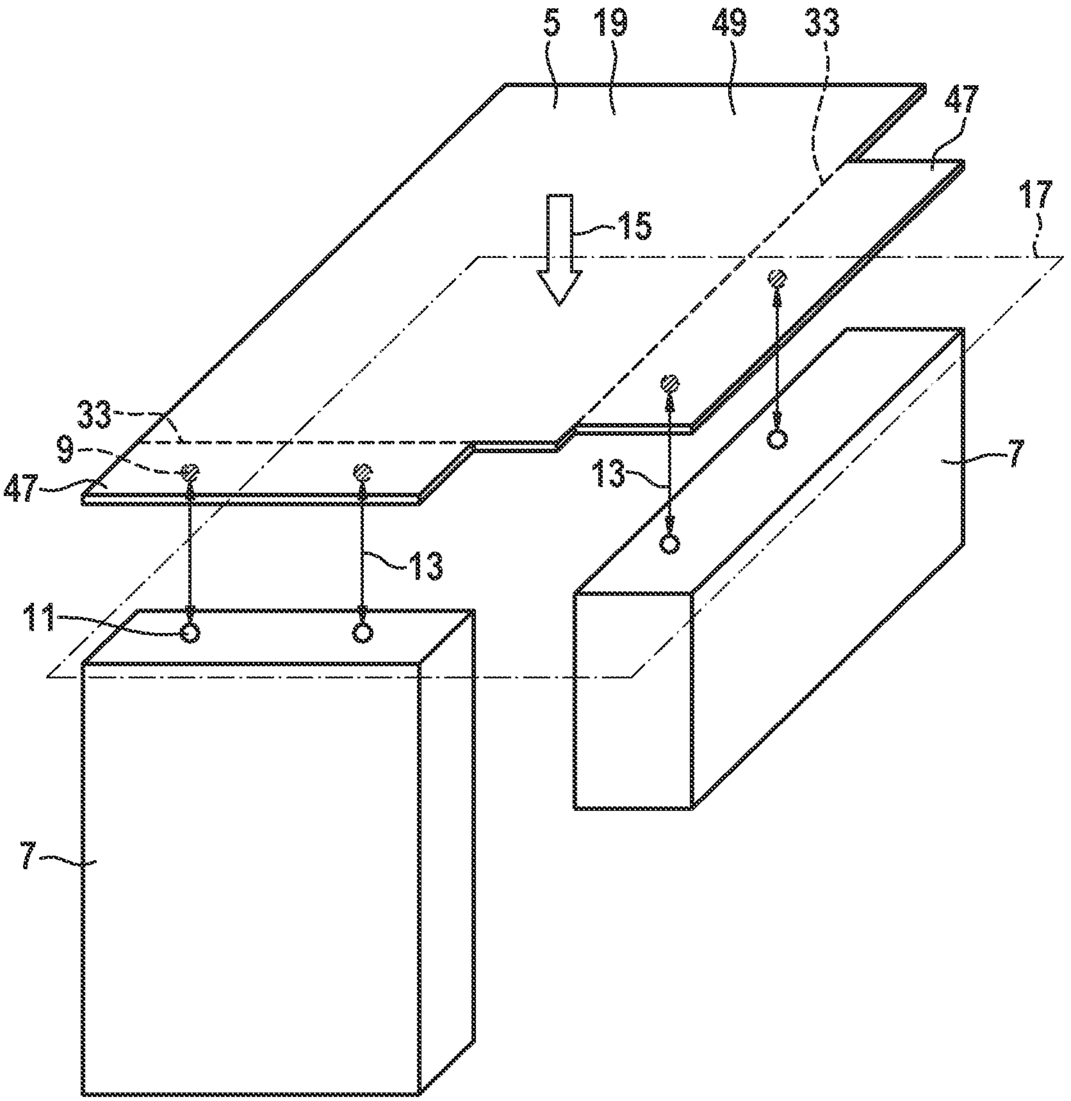
FIG. 3 shows a perspective view onto a first configuration during a fabrication method according to an embodiment of the present invention.

FIG. 3 shows an embodiment in which the electronic module 5 comprises a planar carrier substrate 19. The carrier substrate 19 may be a printed circuit board on which various electronic devices (not shown) are arranged in a central circuitry portion 49. Furthermore, the carrier substrate 19 comprises contact portions 47 at its circumference. Module contacts 9 are arranged in the contact portions 47. A buckling portion 33 extends between the circuitry portion 49 and each of the contact portions 47. At the buckling portion 33, the carrier substrate 19 has a reduced buckling rigidity as compared to the neighbouring contact and circuitry portions 47, 49.

In the first configuration shown in the figure, the carrier substrate 19 is arranged in a vertical initial distance 13 with regard to each of two periphery components 7. Therein, the component contacts 11 of each of the periphery components 7 are arranged in a common plane 17.

Subsequently, the electronic module 5 is displaced about the initial distance 13 along the direction 15 towards the periphery components 7 into the second configuration in which all component contacts 11 directly contact their corresponding module contacts 9.

Figure 4A:
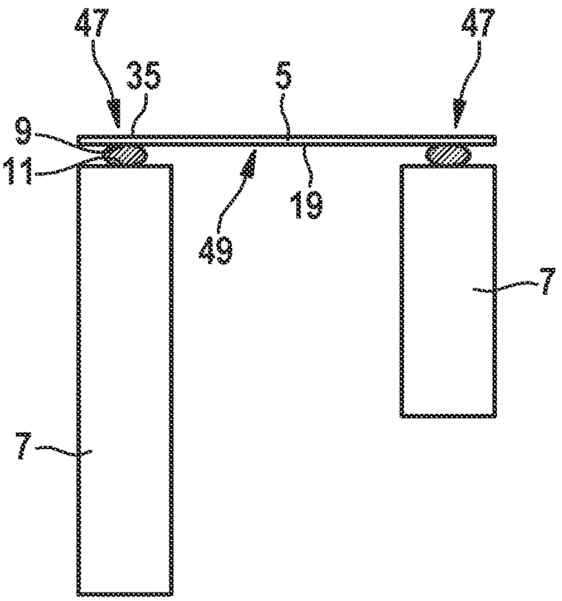
FIGS. 4A-4C visualize a sequence of steps during a fabrication method according to an embodiment of the present invention
Figure 4B:
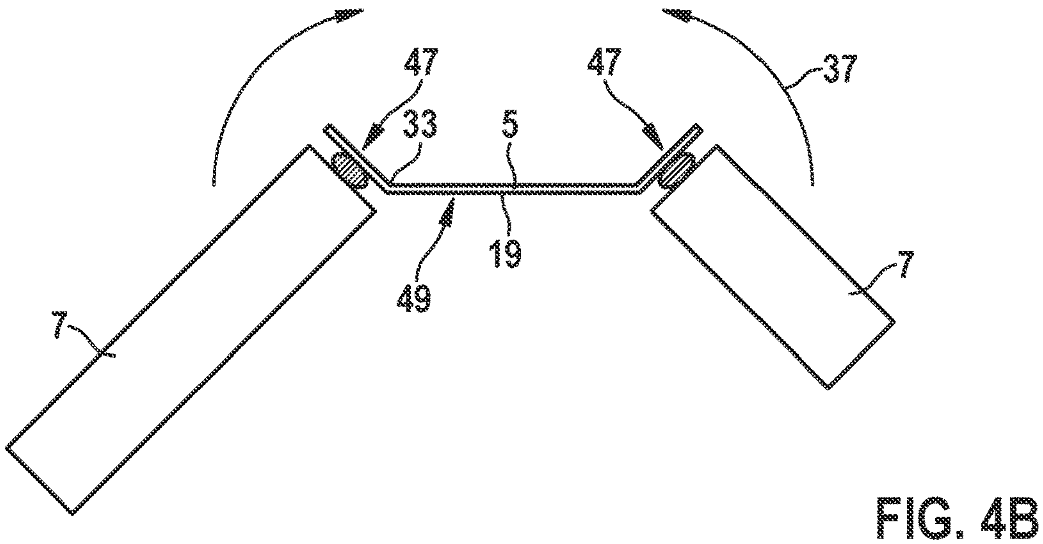
Figure 4C:
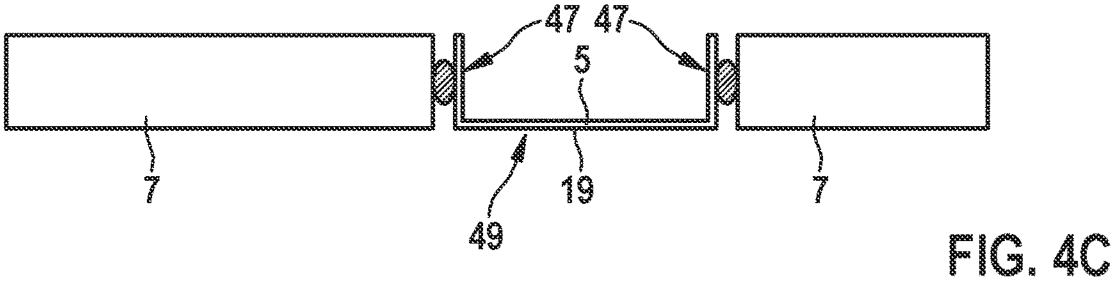

FIGS. 4A-C show a sequence of method steps in which the electronic module 5 and the periphery components 7 are first in their second configuration (FIG. 4A). In this second configuration, the entire carrier substrate 19 is planar.

Subsequently, the periphery components 7 are displaced to another position relative to the electronic component 5 by pivoting the periphery components 7 in a rotation direction 37. Upon such displacement, bending forces are applied to the carrier substrate 19. Due to such bending forces, the buckling portions 33 are successively deformed (FIG. 4B).

Finally, the entire arrangement is deformed into a third configuration in which the periphery components 7 are arranged in another position and another orientation relative to the electronic module 5 as compared to the second configuration (FIG. 4C). Specifically, the periphery components 7 may be arranged such as to extend essentially in a same plane as the electronic module 5. Thereby, an entity comprising the electronic module 5 and plural periphery components 7 may have a shallow shape and may then be accommodated in a shallow housing 3.

Figure 5A:
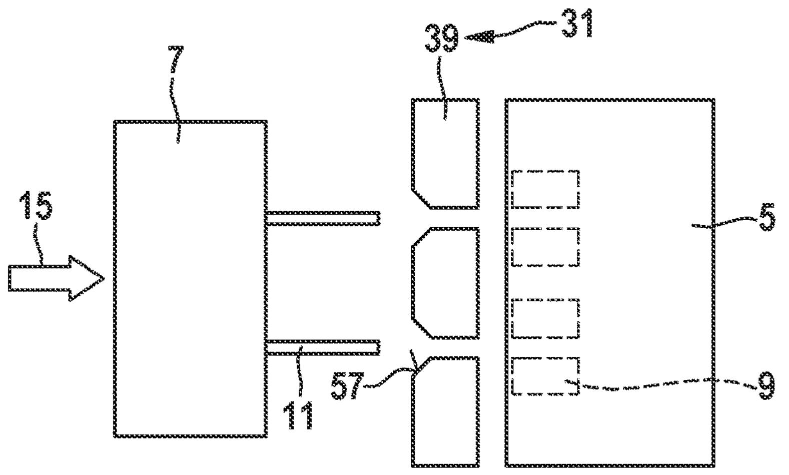
FIGS. 5A-5C show guiding structures applied during a fabrication method according to an embodiment of the present invention.
Figure 5B:
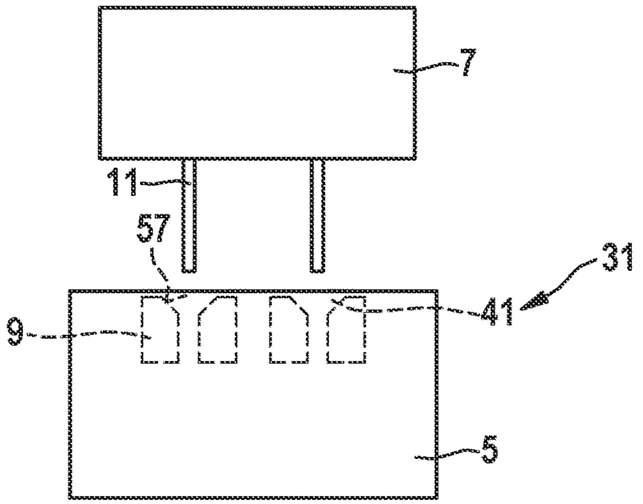
Figure 5C:
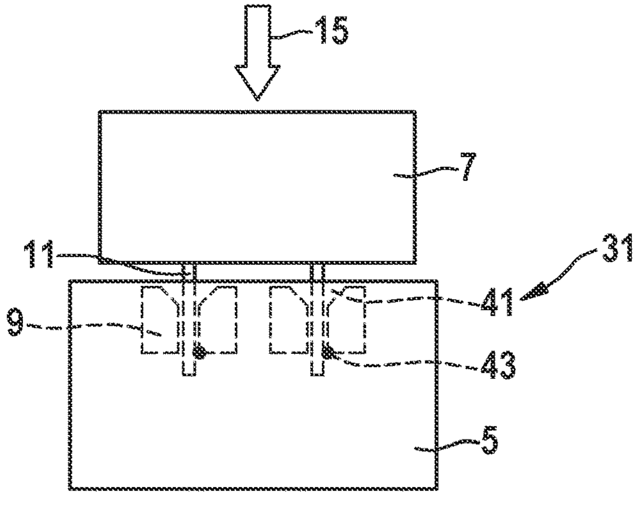

FIGS. 5A-C shows guiding structures 31 used during fabricating a medical device 1. The guiding structures 31 comprise sliding surfaces 57 which are configured and arranged such as to guide the component contacts 11 towards corresponding module contacts 9 upon the displacement along the common direction 15.

In FIG. 5A, an external guiding plate 39 forms the guiding structures 31. The guiding plate 39 is temporarily arranged between the electronic module 5 and the periphery components 7. As soon as the component contacts 11 directly contact and are fixed to the corresponding module contacts 9, the guiding plate 39 may be removed. Alternatively, the guiding plate 39 may remain and may form an integral part of the final medical device.

In FIGS. 5B and C, internal guiding blocks 41 form the guiding structures 31. In the example shown, the guiding blocks 41 are integrated into the electronic module 5 and form a part of the module contacts 9. The guiding blocks 41 form sliding surfaces 57. Upon displacing the periphery components 7 along the common direction 15 towards the electronic module 5, the guiding blocks 41 guide the component contacts 11 with their sliding surfaces 57. Upon being correctly aligned and inserted into the module contacts 9, the component contacts 11 may be fixed, for example, by a welding connection 43.

Figure 6A:
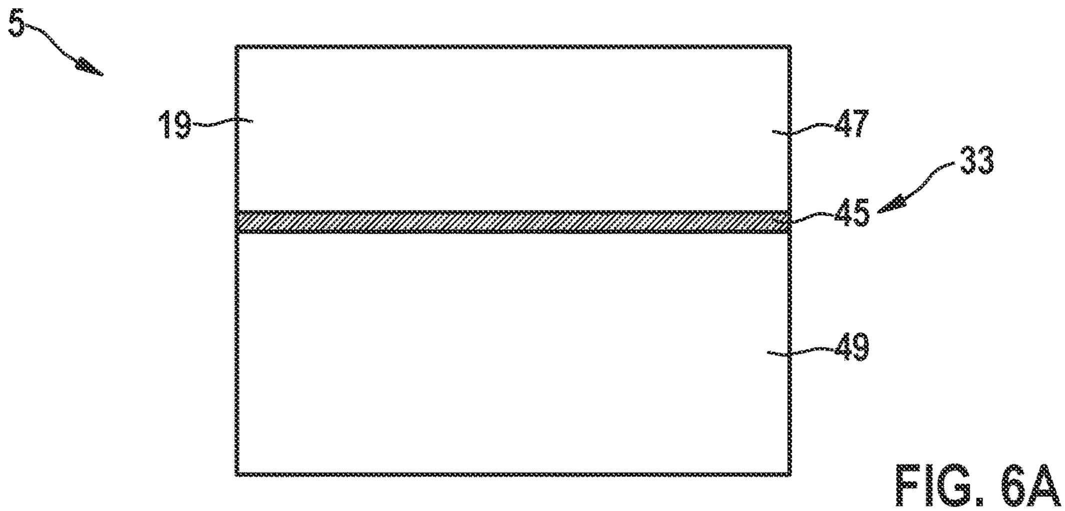
FIGS. 6A-6C show buckling portions of an electronic module of an implantable medical device according to an embodiment of the present invention.
Figure 6B:
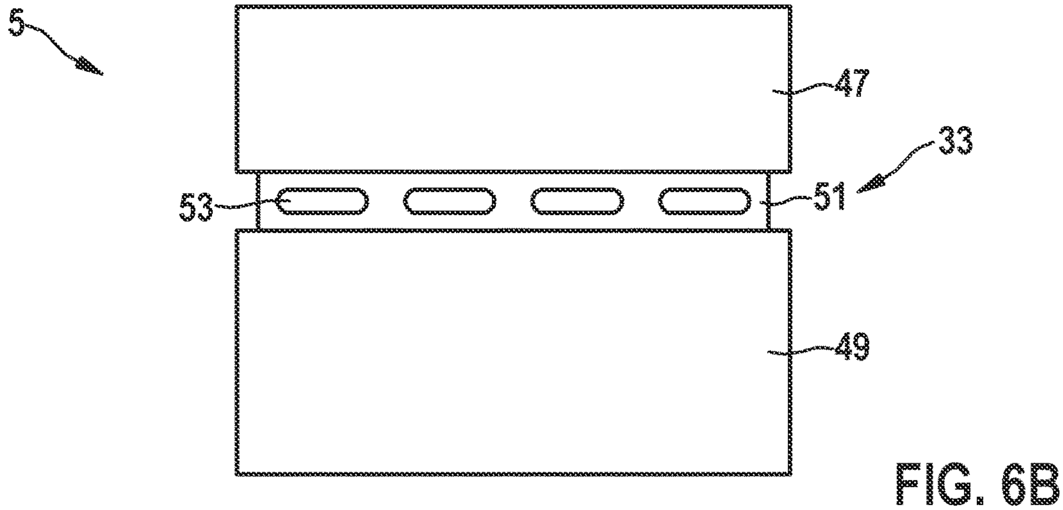
Figure 6C:
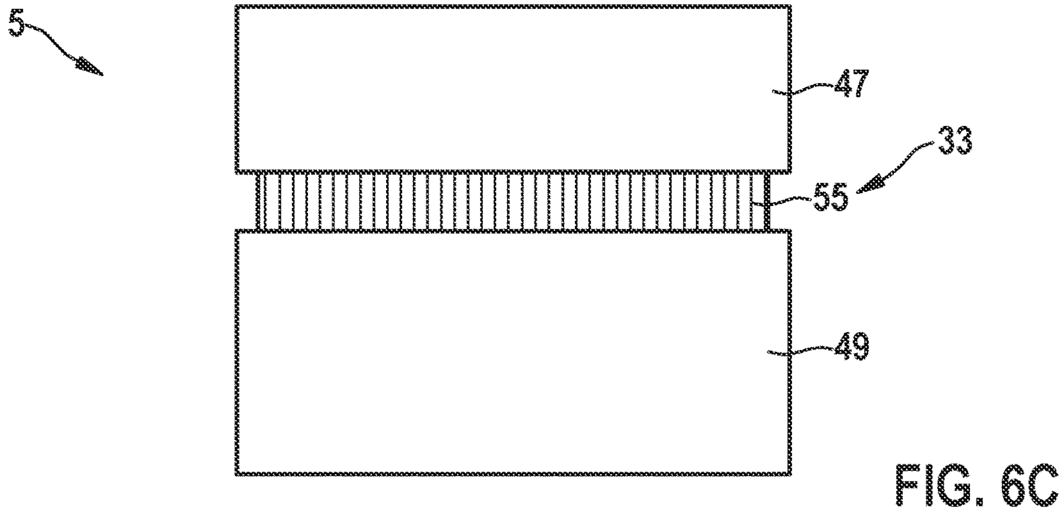

In FIGS. 6A-C, various types of buckling portions 33 in the electronic module 5 are visualised. The buckling portions 33 may extend linearly along a carrier substrate 19 and have a reduced buckling rigidity as compared to neighbouring portions.

In one example, the buckling portion 33 may be formed by a rabbet portion 45 (FIG. 6A). At such rabbet portion 45, a carrier substrate 19 may be locally thinner than in neighbouring contact and circuitry portions 47, 49.

In another example, the buckling portion 33 may be formed by a perforation portion 51 (FIG. 6B). The perforation portion 51 comprises a multiplicity of recesses 53.

In a further example, the buckling portion 33 may be formed with a flexible portion 55 (FIG. 6C). The flexible portion 55 may be formed with a material having a higher flexibility than a material of the adjacent contact and circuitry portions 47, 49.

Figure 7A:
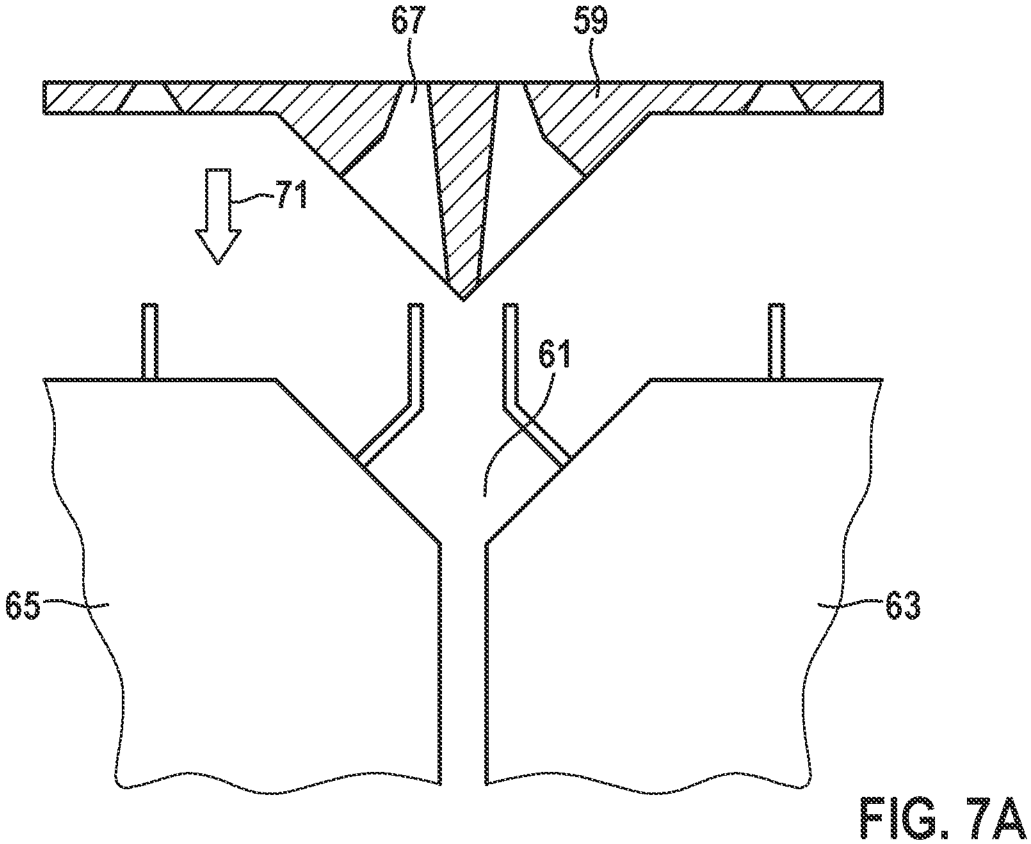
FIGS. 7A-7B show a feeding component allowing an existing concave construction space for arranging components relative to the feeding component of an electronic module of an implantable medical device according to an embodiment of the present invention.
Figure 7B:
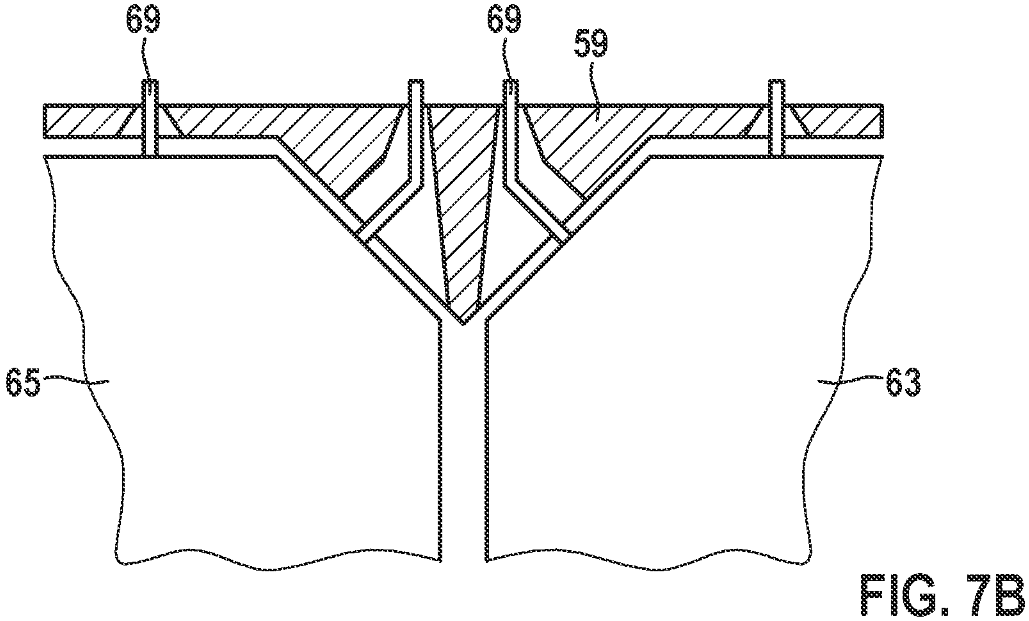

FIGS. 7A and B show an embodiment in which a feeding component 59 is formed such that an existing concave construction space 61 is used for correctly and precisely arranging components 63, 65 relative to the feeding component 59. FIG. 7*a* shows an arrangement before assembly, FIG. 7B shows an arrangement after assembly in a feeding direction 71. The feeding component 59 may be, e.g., the electronic module 5 or a device attached or arranged thereto, and the components 63, 65 may be, e.g., periphery components 7. The construction space 61 may be formed from a concave portion of one or both or several of the components 63, 65. The feeding component 59 comprises cavities 67 having guiding characteristics. For example, the cavities 67 may be converging, i.e., for example, funnel-shaped. Accordingly, contacting elements 69 such as contacts 9 of the components 63, 65 may be guided and aligned with strict tolerances.

Finally, it should be noted that the term "comprising" does not exclude other elements or steps and the "a" or "an" does not exclude a plurality. Also elements described in association with different embodiments may be combined. It should also be noted that reference signs in the claims should not be construed as limiting the scope of the claims.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range, including the end points.

LIST OF REFERENCE NUMERALS

1 implantable medical device
3 housing
5 electronic module
7 periphery component
9 module contact
11 component contact
13 initial distance
15 common direction
17 common plane
19 carrier substrate
21 frame
23 grabber
25 holding arrangement
27 vision system
29 tolerance element
31 guiding structure
33 buckling portion
35 interconnection
37 rotation direction
39 external guiding plate
41 internal guiding block
43 welding connection
45 rabbet portion
47 contact portion
49 circuitry portion
51 perforation portion
53 recess
55 flexible portion
57 sliding surface
59 feeding component
61 concave construction space
63 component
65 component
67 cavities
69 contacting elements
71 feeding direction

The invention claimed is:

1. Method for fabricating an implantable medical device, wherein the method comprises:

providing a housing, an electronic module and a plurality of periphery components, wherein the electronic module comprises module contacts for at least one of inputting electric energy to the electronic module and outputting electric energy from the electronic module, and wherein each of the periphery components comprises component contacts for at least one of inputting electric energy to the periphery component and outputting electric energy from the periphery component;

wherein in a horizontal direction, lateral positions of each periphery component contact at the periphery components are aligned with lateral positions of corresponding module contacts at the electronic module;

arranging the electronic module and the plurality of periphery components in a first configuration in which each of the component contacts of each of the periphery components is positioned at a same initial distance in relation to a corresponding one of the module contacts with regards to a common direction;

displacing the electronic module and the plurality of periphery components by the initial distance relative to each other in a common motion into a second configuration in which all of the component contacts of each of the periphery components directly mechanically contact their respective corresponding module contacts;

fixing the electronic module and the plurality of periphery components in the second configuration; and accommodating the electronic module and the plurality of periphery components in the housing.

2. Method of claim 1, wherein, in the second configuration, all of the component contacts are arranged in a common plane.

3. Method of claim 1, wherein the electronic module comprises a planar carrier substrate and all of the module contacts are arranged at a surface of the carrier substrate.

4. Method of claim 1, wherein at least some of the component contacts and the corresponding module contacts are permanently fixed to each other.

5. Method of claim 1, wherein at least some of the component contacts and the corresponding module contacts are fixed to each other in a releasable manner.

6. Method of claim 1, wherein, in the first configuration, at least some of the periphery components are held by a holding arrangement comprising at least one frame, each frame being adapted for holding a corresponding one of the periphery components in a form-fitting manner.

7. Method of claim 1, wherein, in the first configuration, at least some of the periphery components are held by a holding arrangement comprising grabbers, each grabber being adapted for selectively grabbing and releasing a corresponding one of the periphery components.

8. Method of claim 7, wherein motions of the grabbers are controlled by a vision system.

9. Method of claim 7, wherein the grabbers comprise tolerance elements being configured in a positioning tolerant manner so as to guide the periphery component from the first configuration to the second configuration while allowing an acceptable positioning tolerance.

10. Method of claim 1, wherein, upon the displacing of the electronic module and the plurality of periphery components into the second configuration, guiding structures are provided for guiding the module contacts and the component contacts into coinciding positions.

11. Method of claim 1, the method furthermore comprising:

deforming the electronic module with the plurality of periphery components fixed thereto in the second configuration into a third configuration, wherein, in the third configuration, at least one of the periphery components is arranged at another position relative to the electronic module as compared to the second configuration.

12. Method of claim 11, wherein the electronic module with the plurality of periphery components fixed thereto is deformed into the third configuration by bending at least one portion of the electronic module.

13. Method of claim 11, wherein the electronic module comprises at least one buckling portion having reduced buckling rigidity as compared to neighboring portions of the electronic module, and wherein the electronic module with the plurality of periphery components fixed thereto is deformed into the third configuration by bending the at least one buckling portion.

14. Implantable medical device, comprising:

a housing, an electronic module, and a plurality of periphery components, wherein the electronic module comprises module contacts for at least one of inputting electric energy to the electronic module and outputting electric energy from the electronic module, wherein each of the periphery components comprises component contacts for at least one of inputting electric energy to the periphery component and outputting electric energy from the periphery component, wherein in a horizontal direction, lateral positions of each periphery component contact at the periphery components are aligned with lateral positions of corresponding module contacts at the electronic module, wherein the electronic module and the plurality of periphery components are fixed to each other and all of the component contacts of each of the periphery components directly mechanically contact respective corresponding module contacts, wherein the electronic module comprises at least one buckling portion having reduced buckling rigidity as compared to neighboring portions of the electronic module, and wherein at least one of the periphery components is fixed to the electronic module at a position at a first lateral side of the buckling portion and at least one other of the periphery components is fixed to the electronic module at a position at a second lateral side of the buckling portion.

15. Implantable medical device of claim 14, wherein the electronic module with the plurality of periphery components fixed thereto is configured such that it may be deformed by bending the at least one buckling portion into a configuration in which all of the component contacts are arranged in a common plane.

* * * * *